US00PP33573P2

(12) United States Plant Patent
Bovio

(10) Patent No.: US PP33,573 P2
(45) Date of Patent: Oct. 19, 2021

(54) ***LAMIUM* PLANT NAMED 'ORCHID FROST GRANDE'**

(50) Latin Name: *Lamium maculatum*
Varietal Denomination: Orchid Frost Grande

(71) Applicant: Michael Bovio, White Lake, MI (US)

(72) Inventor: Michael Bovio, White Lake, MI (US)

( * ) Notice: Subject to any disclaimer, the term of this patent is extended or adjusted under 35 U.S.C. 154(b) by 0 days.

(21) Appl. No.: 17/185,218

(22) Filed: Feb. 25, 2021

(51) Int. Cl.
*A01H 5/02* (2018.01)
*A01H 6/00* (2018.01)

(52) U.S. Cl.
USPC ..... Plt./444

(58) Field of Classification Search
USPC ..... Plt./444
CPC ..... A01H 6/00; A01H 5/02
See application file for complete search history.

*Primary Examiner* — Keith O. Robinson
(74) *Attorney, Agent, or Firm* — Weatherly IP Solutions, LLC; James M. Weatherly

(57) ABSTRACT

A new variety of *Lamium* plant named 'Orchid Frost Grande' that is distinguishable by vigorous growth, prostrate well-branched plant habit, heart-shaped leaves which are silver-grey in color and accented by a contrasting dark green marginal variegation and large red-purple inflorescences and individual flowers which are held upright along the stems and also pendulous at the end of the stems, is disclosed.

2 Drawing Sheets

Genus and species: *Lamium maculatum.*
Variety denomination: 'Orchid Frost Grande'.

BACKGROUND

The present disclosure relates to a new and distinct variety of *Lamium* plant, also known as Dead Nettle or Spotted Dead Nettle, a perennial that is grown for use as an ornamental landscape and container plant. The new variety is known botanically as *Lamium maculatum* and will be referred to hereinafter by the variety name 'Orchid Frost Grande'.

The new *Lamium* variety 'Orchid Frost Grande' resulted from chemical treatment of the inventor's variety *Lamium* 'Orchid Frost' (U.S. Plant Pat. No. 11,122). Specifically, Stage II tissue cultured microplants of 'Orchid Frost' were treated in the holding laboratory with a 0.001% solution of the chemical colchicine during February 2019 and observed after 6 months. The laboratory treatments resulted in a range of progeny including probable tetraploid mutations which would require further evaluation in vivo.

In November 2019, the progeny was transferred as unrooted cuttings to a commercial nursery in Oxnard, Calif. where the plants were rooted and grown on, and asexually propagated under the inventor's direction.

In April 2020, the inventor selected the present variety 'Orchid Frost Grande' for its markedly larger inflorescence and individual flowers when compared with the parent variety 'Orchid Frost'. In addition, 'Orchid Frost Grande' bears larger leaves and grows rapidly all of which indicates to the inventor that 'Orchid Frost Grande' is a tetraploid variety.

'Orchid Frost Grande' was first asexually propagated in January 2020 in a greenhouse in Oxnard, Calif. The inventor has confirmed that 'Orchid Frost Grande' is stable and reproduces true to type in successive generations of asexual reproduction.

SUMMARY

The following traits have been repeatedly observed and represent the distinguishing characteristics of 'Orchid Frost Grande'. 'Orchid Frost Grande' has not been tested under all possible conditions and phenotypic differences may be observed with variations in environmental, climatic, and cultural conditions, without however, any variance in genotype.

1. 'Orchid Frost Grande' exhibits a prostrate well-branched plant habit.
2. The leaves of 'Orchid Frost Grande' are heart-shaped and silver-grey in color, accented by a contrasting uniformly dark green marginal variegation.
3. 'Orchid Frost Grande' grows and flowers rapidly. Flowering plants may be produced in 10 to 12 weeks from a cutting.
4. The inflorescences of 'Orchid Frost Grande' are large and held upright along the stems and pendulous at the end of the stems.
5. The buds and flowers of 'Orchid Frost Grande' are dark red-purple in color.
6. 'Orchid Frost Grande' may be grown and used as a perennial in the garden or landscape, or as a ground cover, or planted in mixed containers for year-round foliage effect and flowering from spring to fall.

DESCRIPTION OF THE PHOTOGRAPHS

The accompanying color photographs illustrate the overall appearance of the new *Lamium* variety 'Orchid Frost Grande' showing the colors as true as it is reasonably possible to obtain in colored reproductions of this type. Photographs were taken in April 2020 in Oxnard, Calif. from a five months old plant grown outdoors in a 3-gallon container, with one pinch after initial cutting establishment and without any chemical growth regulators. Colors in the photographs may differ from the color values cited in the detailed botanical description, which more accurately describes the actual colors of the new variety 'Orchid Frost Grande'.

DESCRIPTION OF THE NEW VARIETY

Figure 1:
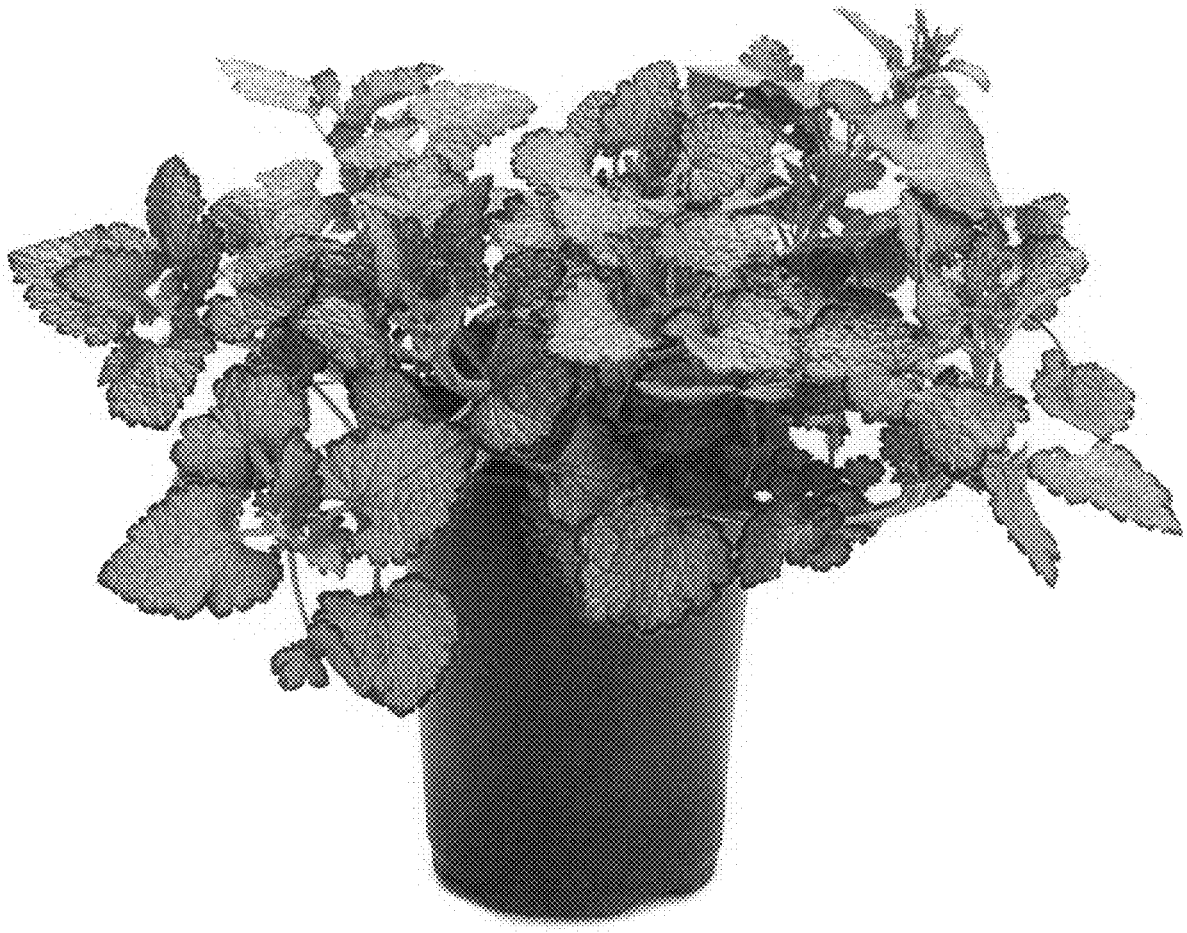
FIG. 1 depicts an entire plant in flower of 'Orchid Frost Grande'.
Figure 2:
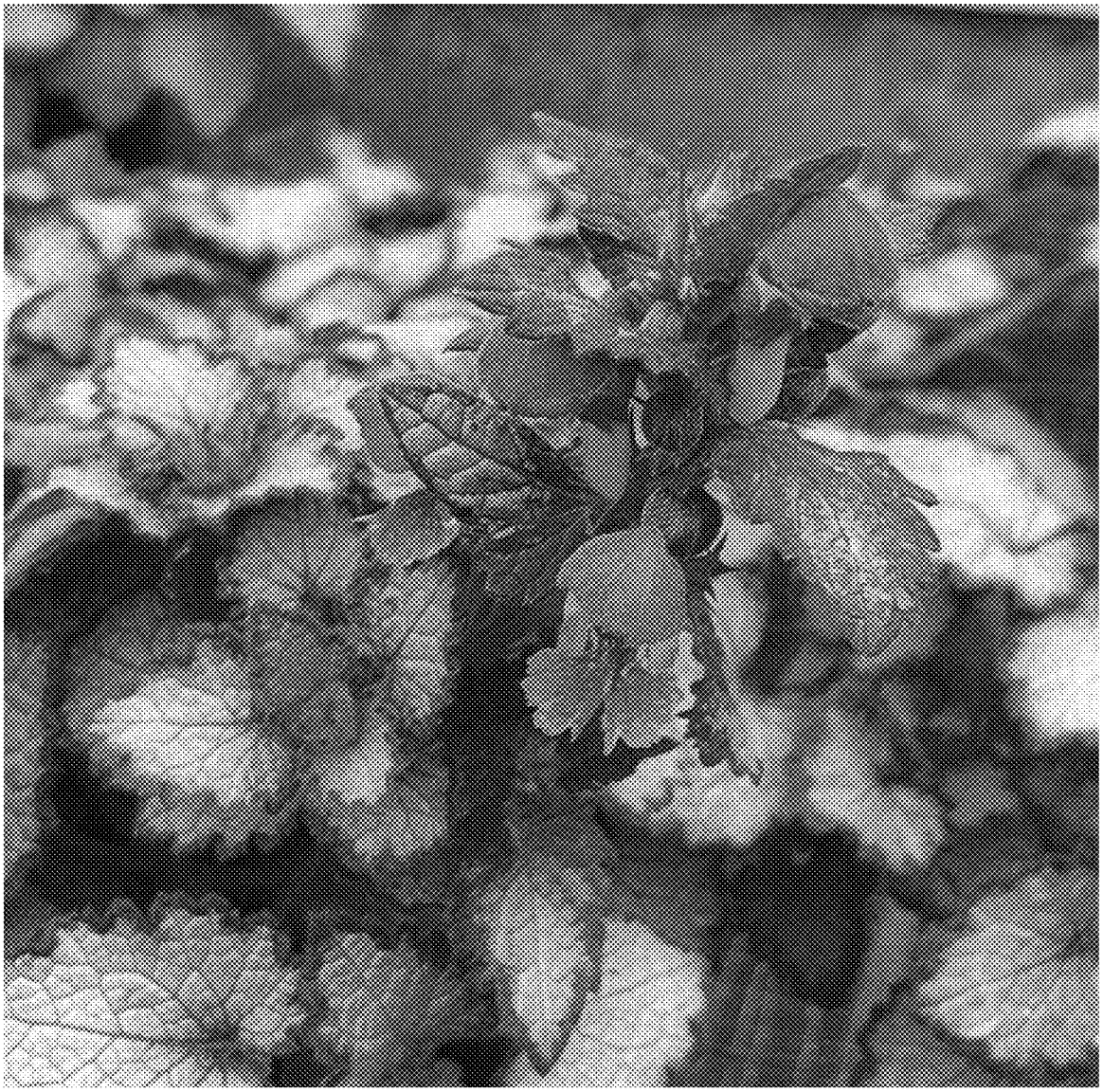
FIG. 2 depicts a close-up view of an inflorescence of 'Orchid Frost Grande'.

The following detailed descriptions set forth the distinctive characteristics of 'Orchid Frost Grande'. Observations, measurements, values, and comparisons were collected in April 2020 in Santa Barbara, Calif. from a five months old plant which had been growing outdoors in full sun in a 3 gallon container in Oxnard, Calif., with one pinch after initial cutting establishment and without any chemical growth regulators. Color determinations were made in accordance with The 2007 Royal Horticultural Society Colour Chart from London England, except where general color terms of ordinary dictionary significance are used.

Classification:

*Family*.—Lamiaceae.

*Genus*.—*Lamium*.

*Species*.—*Maculatum*.

*Common name*.—Dead Nettle, or Spotted Dead Nettle.

Parentage: 'Orchid Frost Grande' arose as a chemically induced mutation of the inventor's variety of *Lamium* plant named 'Orchid Frost'.

Plant:

*Propagation method*.—Softwood tip cuttings.

*Rooting system*.—Fine and fibrous.

*Vigor*.—Moderate vigor.

*Time to develop roots*.—5 days are needed for a cutting to develop roots at recommended rooting temperature of 20° to 22° Centigrade.

*Crop time*.—Approximately 10 to 12 weeks are required to produce a budded and flowering plant from planting a rooted cutting.

*Suggested container sizes*.—Small cell or plug plants for mass planting or transplanting into larger containers or mixed containers. Larger containers up to 5 gallons are suitable for producing specimen plants for the garden and landscape.

*Use*.—Versatile and suited to most climates as a garden or landscape plant, including ground cover, and for use in mixed planted containers.

*Type*.—Perennial.

*Overall dimensions*.—After 5 months growth, 20 cm in height, including the inflorescence, and 35 cm in width.

*Cultural requirements*.—Grow in full sun with moderate water and well-draining soil.

*Hardiness*.—USDA Zone 4.

*Form and growth habit*.—Predominantly dense prostrate foliage with inflorescences held above the foliage canopy and pendulously at the branch terminals.

*Blooming seasons*.—Spring, summer and fall.

*Lastingness of blooms*.—Inflorescence has some flower for 14 days, newly-opened individual flowers last for 2 to 3 days.

Branches:

*Quantity*.—8 to 12.

*Shape*.—Square.

*Length*.—20 to 25 cm. measured to base of inflorescence.

*Width*.—4 to 5 mm towards the base tapering to 3 mm immediately below the inflorescence.

*Internode length*.—2 cm to 4 cm.

*Color*.—143C.

*Texture*.—Rough, pubescent, hairs fine, length up to 2 mm, color white NN155C.

Leaves:

*Type, arrangement*.—Simple, opposite.

*Attachment*.—Petiolate.

*Quantity per branch*.—5 to 7 pairs.

*Shape*.—Cordate.

*Length*.—48 mm.

*Width*.—55 mm.

*Margin*.—Dentate, 6 to 7 teeth on each side edge, depth 3 to 4 mm, hairs fine, <0.5 mm in length, color NN155C.

*Venation*.—Pinnate, adaxial veins depressed, abaxial veins raised.

*Texture*.—Adaxial surface: Glabrous, glossy. Abaxial surface: Glabrescent.

*Variegation*.—Prominent and present on adaxial surface only.

*Leaf color* (*both surfaces*).—Except for 3 to 4 leaves immediately below the inflorescence, NN155D with narrow dark green edge.

*Leaf edge*.—Extends 2 mm inwards from margin, color 136A.

*Leaf color* (3 *to* 4 *leaves immediately below inflorescence, both surfaces*).—136A with occasional splashes NN155D.

*Apex*.—Acute.

*Base*.—Cuneate.

*Fragrance*.—As wild nettles when rubbed.

*Stipules*.—Present in one or two pairs at each leaf axil. Small, petiolate cordate leaflets up to 1.5 cm in length and width. All other characteristics same as leaves (including variegation).

Petiole:

*Shape*.—Sulcate.

*Length*.—3.5 cm.

*Width*.—2 mm.

*Texture*.—Puberulent.

*Color*.—143C.

Inflorescence:

*Type*.—Verticillaster. Peduncle absent.

*Number of inflorescences per plant at maturity*.—20 to 30.

*Dimensions*.—Ranges between 4 cm in height and diameter, to 6 cm in height and 5 cm in diameter.

Calyx:

*Position*.—Sessile.

*Shape*.—Campanulate, flared toward the apex.

*Length*.—8 mm to 10 mm.

*Width*.—12 mm across flared apex.

Sepals:

*Quantity*.—5, fused at base, otherwise free, divergent.

*Sepal length* (*free*).—5 mm to 6 mm.

*Width*.—6 mm when flattened.

*Shape* (*where free*).—Narrow lanceoloate.

*Apex*.—Acuminate.

*Base*.—Truncate.

*Margin*.—Entire.

*Surface texture* (*both surfaces*).—Glabrous.

*Color*.—Adaxial surface (fused base): 144B. Adaxial surface (free sepals): 141B. Abaxial surface: 144B.

Flowers:

*Type*.—Zygomorphic, axillary, single, arranged in verticillasters.

*Quantity*.—20 to 25 per inflorescence.

*Shape*.—Corolla tube clavate, flowers present upper petal as a hemispherical hood and lower petals and lobes as lower lips.

*Fragrance*.—None observed except for secreted sweet-smelling nectar.

Bud:

*Shape*.—Globose.

*Diameter*.—7 mm.

*Texture*.—Densely pubescent, almost furry. Hairs very fine, white NN155C, 1 mm in length.

*Color*.—71A.

Corolla:

*Shape*.—Tubular and curved upwards as tube emerges from calyx.

*Length*.—15 mm, including corolla tube, length 12 mm.

*Width* (*measured vertically*).—5 mm.

*Width* (*measured horizontally*).—2 to 3 mm.

*Texture* (*both surfaces*).—Glabrous, abaxial surface glandular and sticky with colorless nectar.

*Color* (*except tube, both surfaces*).—70B.

*Color* (*corolla tube, both surfaces*).—NN155B, translucent.

Petals:

*Quantity*.—2.

*Arrangement*.—One upper petal (hood), one lower petal which appears as a prominent two-lobed lip facing downward and outward.

*Upper petal*.—Shape: Hooded, hemispherical. Width and height: 18 to 20 mm. Texture: Adaxial surface: Densely pubescent, hairs fine, length<0.5 mm, color NN155C. Abaxial surface: Glabrous. Apex: Rounded. Base: Truncate. Upper petal, lower petal basally fused to corolla tube. Margin: Smooth, wavy, entire. Upper petal color (both surfaces): 71C.

*Lower petal*.—Shape: Two adjacent rhomboid lobes, fused at base. Length (each lobe): 7 mm. Width (each lobe): 6 mm. Texture (both surfaces): Smooth, glabrous. Apex: Broad, undulating with occasional notches, depth 0.5 to 1.0 mm. Base: Truncate. Margin: Entire, gently undulating. Color (both surfaces): 71C, N74D, and N155D all individually present.

*Floral bracts*.—Present as 2 to 3 claw-like bracts attached to margin above each of the lower petal lobes; 2 mm in length, 0.5 mm in width, color 70B.

Reproductive organs:

*Stamens*.—Quantity: 4. Filaments parallel, fused at base, length 25 mm, diameter 1 mm, color NN155D.

*Anther*.—Shape: Double ellipsoid, basally fused and attached to filament. Length: 3 mm. Width: 1 mm. Color: 187A.

*Pollen*.—Amount: Light. Color: N167B.

*Pistil*.—Quantity: 1. Style: length 25 mm, color NN155D (identical to filaments). Stigma: Forked (bifid), each fork 2-3 mm in length and slightly recurving.

*Ovary* (*only observed unfertilized*).—Position: Superior, appears as domed pinhead, 1.5 mm in diameter, color 196B.

Seed: None observed.

Disease and pest susceptibility: Susceptible to aphids (*Aphis gossypii*) and to deer and rabbit grazing. Generally outgrows most bacterial and viral infections.

Drought tolerance: Drought tolerant.

COMPARISON WITH PARENTAL LINES AND CLOSEST KNOWN VARIETY

In comparison with the parent, 'Orchid Frost', which is also the closest variety known to the inventor, 'Orchid Frost Grande' grows more rapidly, is more vigorous and bears inflorescences and flowers which are approximately twice as large. This vigor is attributed to the presumed tetraploid constitution of 'Orchid Frost Grande' and is its distinguishing characteristic.

COMPARISON WITH CO-PENDING VARIETY, *LAMIUM* PLANT NAMED 'ORCHID FROST GOLD'

Whereas the leaves of 'Orchid Frost Gold' are lime green in color with wide mid-green edges, the leaves of 'Orchid Frost Grande' are silver-white in color and exhibit narrower dark green edges. In addition, the flowers and buds of 'Orchid Frost Gold' are smaller and paler red-purple in color than the darker red-purple buds and flowers of 'Orchid Frost Grande'.

I claim:

1. A new and distinct variety of *Lamium* plant named 'Orchid Frost Grande' as described and illustrated herein.

* * * * *